United States Patent
Jeong et al.

(10) Patent No.: US 10,016,351 B2
(45) Date of Patent: Jul. 10, 2018

(54) COMPOSITION FOR PROMOTING HAIR GROWTH OR PREVENTING HAIR LOSS

(71) Applicant: NEOPHARM CO., LTD., Daejeon (KR)

(72) Inventors: Se Kyoo Jeong, Daejeon (KR); Jong Hwan Bae, Daejeon (KR); Bu Mahn Park, Daejeon (KR); Dae Hwan Kim, Daejeon (KR)

(73) Assignee: NEOPHARM CO., LTD., Daejeon (KR)

( * ) Notice: Subject to any disclaimer, the term of this patent is extended or adjusted under 35 U.S.C. 154(b) by 0 days.

(21) Appl. No.: 15/519,822

(22) PCT Filed: Nov. 11, 2015

(86) PCT No.: PCT/KR2015/012099
§ 371 (c)(1),
(2) Date: Apr. 17, 2017

(87) PCT Pub. No.: WO2016/085160
PCT Pub. Date: Jun. 20, 2016

(65) Prior Publication Data
US 2017/0239164 A1    Aug. 24, 2017

(30) Foreign Application Priority Data

Nov. 28, 2014 (KR) .......... 10-2014-0168171
Jul. 20, 2015 (KR) .......... 10-2015-0102490
Jul. 20, 2015 (KR) .......... 10-2015-0102521

(51) Int. Cl.
| A61K 8/68 | (2006.01) |
| A61Q 7/00 | (2006.01) |
| A61Q 5/02 | (2006.01) |
| A61K 8/49 | (2006.01) |
| A61C 7/00 | (2006.01) |

(52) U.S. Cl.
CPC .......... *A61K 8/68* (2013.01); *A61C 7/00* (2013.01); *A61K 8/4953* (2013.01); *A61Q 5/02* (2013.01)

(58) Field of Classification Search
CPC .......... A61K 8/68; A61K 8/4953; A61Q 5/02; A61Q 7/00
USPC .......... 514/275
See application file for complete search history.

(56) References Cited

U.S. PATENT DOCUMENTS

| 3,382,247 | A | 5/1968 | Anthony et al. |
| 5,215,894 | A | 6/1993 | Arison et al. |
| 6,051,698 | A * | 4/2000 | Janjic .......... 435/6.16 |
| 7,253,296 | B2 * | 8/2007 | Darteil .......... C07C 323/52 554/101 |
| 2006/0035977 | A1 * | 2/2006 | Najib .......... A61K 31/131 514/599 |

FOREIGN PATENT DOCUMENTS

| JP | 2006518358 A | 8/2006 |
| KR | 1020010109607 A | 12/2001 |
| KR | 1020080027526 A | 3/2008 |
| KR | 1020120043167 A | 5/2012 |
| KR | 1020130092256 A | 8/2013 |

OTHER PUBLICATIONS

ISA Korean Intellectual Property Office, International Search Report Issued in Application No. PCT/KR2015/012099, dated Oct. 12, 2016, WIPO, 4 pages.

* cited by examiner

*Primary Examiner* — Yevgeny Valenrod
(74) *Attorney, Agent, or Firm* — McCoy Russell LLP

(57) ABSTRACT

The present invention relates to a composition for promoting hair growth or preventing hair loss and, specifically, to a composition, which has excellent stability for skin and no side effects, promotes hair growth, prevents hair loss through the delay of hair loss, and has an excellent hair growth effect.

7 Claims, 2 Drawing Sheets

COMPOSITION FOR PROMOTING HAIR GROWTH OR PREVENTING HAIR LOSS

CROSS-REFERENCE TO RELATED APPLICATIONS

The present application is a U.S. National Phase of International Patent Application Ser. No. PCT/KR2015/012099, entitled "COMPOSITION FOR PROMOTING HAIR GROWTH OR PREVENTING HAIR LOSS," filed on Nov. 11, 2015. International Patent Application Serial No. PCT/KR2015/012099 claims priority to Korean Patent Application No. 10-2014-0168171, filed on Nov. 28, 2014; and to Korean Patent Application No. 10-2015-0102490, filed on Jul. 20, 2015; and to Korean Patent Application No. 10-2015-0102521, filed on Jul. 20, 2015. The entire contents of each of the above-cited applications are hereby incorporated by reference in their entirety for all purposes.

TECHNICAL FIELD

The present invention relates to a composition for promoting hair growth or preventing hair loss, and more specifically, to a composition which has excellent stability to skin, has no side effects, and exhibits excellent effects of hair loss prevention and hair growth by promoting hair growth and delaying hair loss.

BACKGROUND ART

A main cause of hair loss is a genetic factor. However, recently, people suffering from hair loss have gradually increased due to environmental pollution, westernized dietary habits such as processed foods, frequent perming and dyeing, bad scalp care, etc., in addition to an increase in social stress.

Hair is maintained by repeating hair growth and hair loss in a cycle of anagen, catagen and telogen. Specifically, the cycle may be divided into the anagen in which hair grows, the catagen in which growth is completed and a hair bulb part is reduced, the telogen in which papilla stops an activity and hair is maintained on the scalp, and a development stage in which the papilla starts the activity or generates new hair to replace old hair.

A period of the anagen of hair is about three to five years for a man, and four to six years for a woman, and a period of the catagen is about 30 to 45 days, and a period of the telogen is about three to four months, and accordingly, hair loss is naturally caused. In addition, at the end of the telogen, the development stage that new hair is generated starts.

The hair loss is a normal phenomenon. However normal people have a large number of hairs in an anagen state, and on the contrary, people with alopecia have a large number of hairs in the telogen state, such that a hair loss phenomenon is visually noticeable.

People with alopecia are characterized by miniaturization of hair. As hair loss proceeds, a period of the anagen is reduced, and accordingly, the miniaturization of hair also proceeds. Therefore, in order to treat hair loss, it is important to induce hair follicles from the telogen into the anagen quickly, and to increase shorten anagen.

Male pattern alopecia is a phenomenon caused by the male hormone called testosterone which is a hormone that shows male sexual characteristics and helps with the development of muscle, development of male organs, etc., in adolescence. When this testosterone is changed into stronger dihydrotestosterone (DHT) by 5 α-reductase, this hormone acts on the hair follicles by inducing the hair follicles from the anagen into the catagen, such that hair loss is caused. Therefore, in order to treat alopecia caused by the above reason, a method of inhibiting production of DHT by 5 α-reductase is mainly used.

Female pattern alopecia is mainly caused by reduction of an amount of estrogen after menopause. In the female pattern alopecia, hair loss does not occur in a front part of a head, but mainly occurs in a middle part of a head, which is unlike the male pattern alopecia. An effect of 5 α-reductase on the female pattern alopecia is smaller than that on the male pattern alopecia. Therefore, drugs inhibiting 5 α-reductase are not significantly effective for women with alopecia after menopause. Accordingly, minoxidil or estrogen is primarily used as therapeutic agents for alopecia.

Alopecia areata is caused by autoimmune diseases, mental stress, or genetic predisposition. The alopecia areata includes circular or ovoid hair loss and ringworm or trichotillomania. A cause of the alopecia areata is fundamentally different from that of androgenetic alopecia, and a treatment method thereof is also different from that of androgenetic alopecia, and accordingly, a method of treating adrenocortical hormone is used, or a method of applying minoxidil to an affected area or artificially causing stimulation to the affected area is used.

With regard to various and complex causes of hair loss as described above, currently known hair loss prevention products including components that aim at promoting blood circulation, inhibiting male hormone action, enhancing hair root function, etc., as active components, are being sold on the market. However, among them, products having appreciable effect do not exist yet, and side effects are raised in most of products.

As hair growth products, Minoxidil (U.S. Pat. No. 3,382,247) was initially developed and used for the purpose of promoting blood circulation, and then proved a hair growth effect as a side effect among patients using Minoxidil, and after that, received approval from the U.S. Food and Drug Administration (FDA) as raw material for hair growth. Even now, Minoxidil has been used as a therapeutic agent for hair growth. Finasteride (Merck, U.S. Pat. No. 5,215,894) was initially used as a prostate treatment for men, but has also been used as a therapeutic agent for male pattern alopecia by controlling a dose in a human body.

However, it has been reported that Minoxidil has side effects such as stickiness and skin irritation, and Finasteride which is orally administered at present has side effects such as sexual dysfunction, etc., depending on its intake, and is effective for hair loss only when being steadily taken. In addition, the effect may not be expected when applying 5 α-reductase activation inhibitors thereof, but be expected only when orally administrating 5 α-reductase activation inhibitors thereof, such that there are a lot of inconvenience in use.

In consideration of these above-described problems, the present inventors made an effort to provide a composition for external application which is useful for preventing hair loss and promoting hair growth by including a novel compound that prevents signs of skin damage and skin aging to stimulate hair growth factors, thereby producing a hair shaft, promoting hair growth, and delaying hair loss to have a hair growth effect.

DISCLOSURE

Technical Problem

An object of the present invention is to provide a composition which is harmless to a human body, has no side effects, and has excellent effects of hair growth and hair fostering while preventing skin dryness and skin aging.

Technical Solution

In one general aspect, a composition for promoting hair growth or preventing hair loss includes: a derivative represented by Chemical Formula 1 below, a pharmaceutically acceptable salt thereof, or a solvate thereof, as an active component:

[Chemical Formula 1]

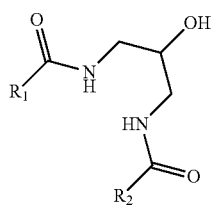

in Chemical Formula 1, $R_1$ and $R_2$ are hydrogen, linear or branched (C7-C30) alkyl, (C7-C30)alkenyl or (C7-C30)alkynyl, wherein the alkyl, alkenyl or alkynyl may be further substituted with hydroxy, carbonyl, (C7-C30)aryl, (C7-C30)aryloxy, (C1-C30)alkylamino, di(C1-C30)alkylamino or amino(C1-C30) alkyl.

The sum of the number of carbons of $R_1$ and $R_2$ may be 4 to 50.

The Chemical Formula 1 may be selected from the following compounds:

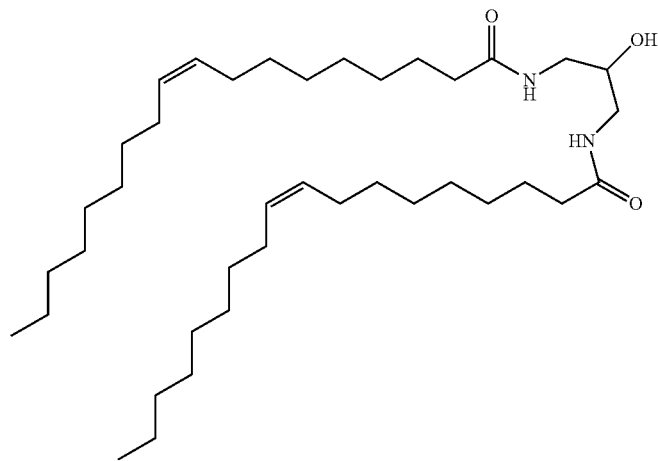

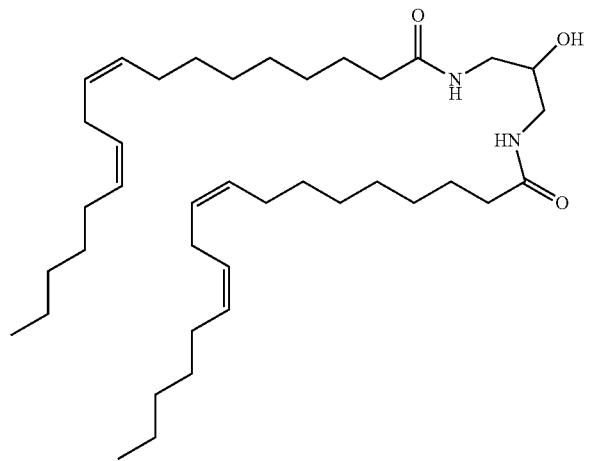

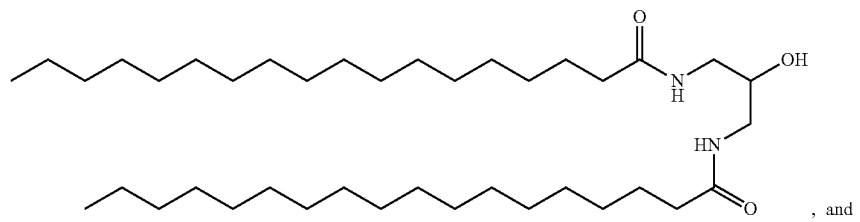

, and

-continued

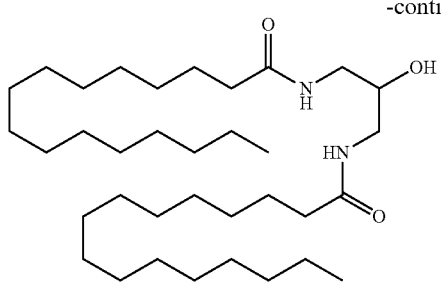

The composition may further include: a pyrimidine oxide derivative or a pharmaceutically acceptable salt thereof.

The pyrimidine oxide derivative may be any one or two selected from 6-(piperidinyl)-2,4-pyrimidinediamine-3-oxide, or 2,4-diamino-6-pyrrolidino-pyrimidine-3-oxide.

The derivative represented by Chemical Formula 1 and the pyrimidine oxide derivative may be included at 1:0.1 to 10.

The composition may contain the derivative represented by Chemical Formula 1, the pharmaceutically acceptable salt thereof, or the solvate thereof as 0.01 to 10 wt % of the active component.

The composition may be a pharmaceutical composition or a cosmetic composition.

The composition may be a skin external formulation including solution, cream, ointment, paste, aerosol agent, gel or wax form, or a hair external formulation including shampoo, rinse, ampoule or treatment form.

Advantageous Effects

The composition according to the present invention contains a novel compound further including a pyrimidine oxide derivative, as a composite active component, such that it is not harmful to the human body even when used daily, has no side effects, is usable continuously for a long period of time, and has an excellent effect of hair growth promotion or hair loss prevention by significantly promoting hair growth. Further, the composition exhibits an effect of relieving inflammation as well as an effect of promoting hair growth.

BEST MODE

Figure 1:
FIG. 1A and FIG. 1B illustrate an effect of promoting hair growth of a composition for hair growth prepared according to an exemplary embodiment of the present invention, i.e., images obtained by observing hair growth of mice.
Figure 2:
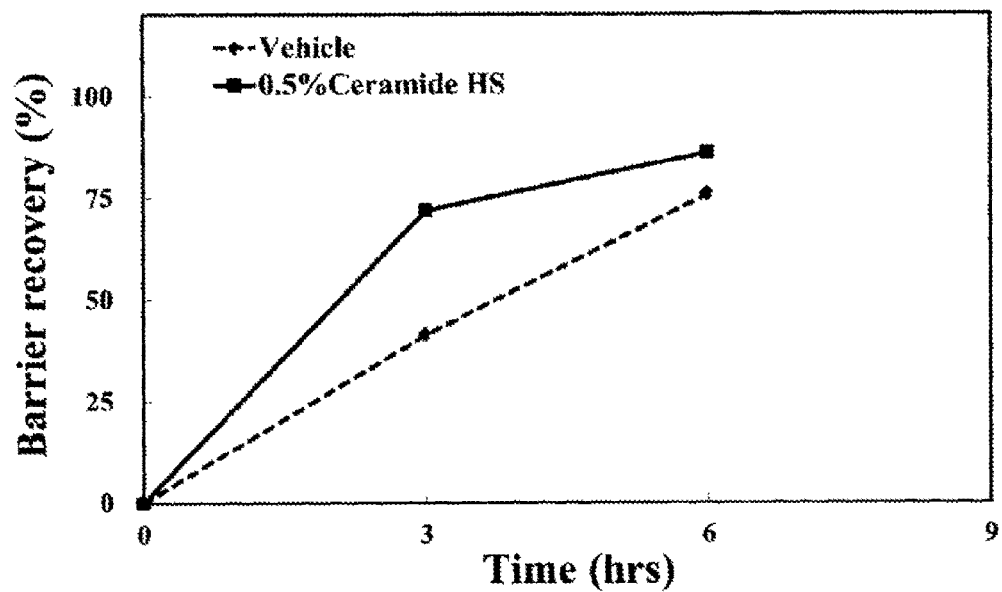
FIG. 2 illustrates an effect of relieving skin barrier damage of the composition for hair growth prepared according to an exemplary embodiment of the present invention.

Hereinafter, composition according to exemplary embodiments of the present invention will be described in detail with reference to the accompanying drawings. Here, unless technical and scientific terms used herein are defined otherwise, they have meanings generally understood by those skilled in the art to which the present invention pertains. Known functions and components which unnecessarily obscure the gist of the present invention in the following description and the accompanying drawings will be omitted.

The present applicant repeated studies on a material which is harmless to a human body, has no side effects, and has an excellent effect of hair growth, and as a result, found that hair growth was significantly promoted and hair loss was prevented by using a composition containing a novel compound further including a pyrimidine oxide derivative, as a composite active component, the novel compound being developed by the present applicant, and completed the present invention.

The composition according to the present invention is a composition for promoting hair growth or preventing hair loss, and contains a derivative represented by Chemical Formula 1 below, a pharmaceutically acceptable salt thereof, or a solvate thereof, as an active component:

[Chemical Formula 1]

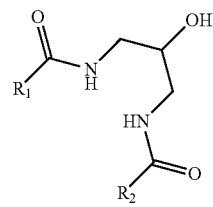

in Chemical Formula 1, $R_1$ and $R_2$ are hydrogen, linear or branched (C7-C30)alkyl, (C7-C30)alkenyl or (C7-C30)alkynyl, wherein the alkyl, alkenyl or alkynyl may be further substituted with hydroxy, carbonyl, (C7-C30)aryl, (C7-C30)aryloxy, (C1-C30)alkylamino, di(C1-C30)alkylamino or amino(C1-C30)alkyl.

Preferably, $R_1$ and $R_2$ may be hydrogen, linear or branched (C7-C30)alkyl, (C7-C30)alkenyl having one or two double bonds or (C7-C30)alkynyl having one or two triple bonds, but are not limited thereto.

In addition, in the derivative represented by Chemical Formula 1 as an example of the present invention, the sum of the number of carbons of $R_1$ and $R_2$ is preferably 4 to 50, and more preferably, 30 to 40, but is not limited thereto.

For example, the Chemical Formula 1 of the present invention is the most preferably selected from the following compounds, but is not limited thereto:

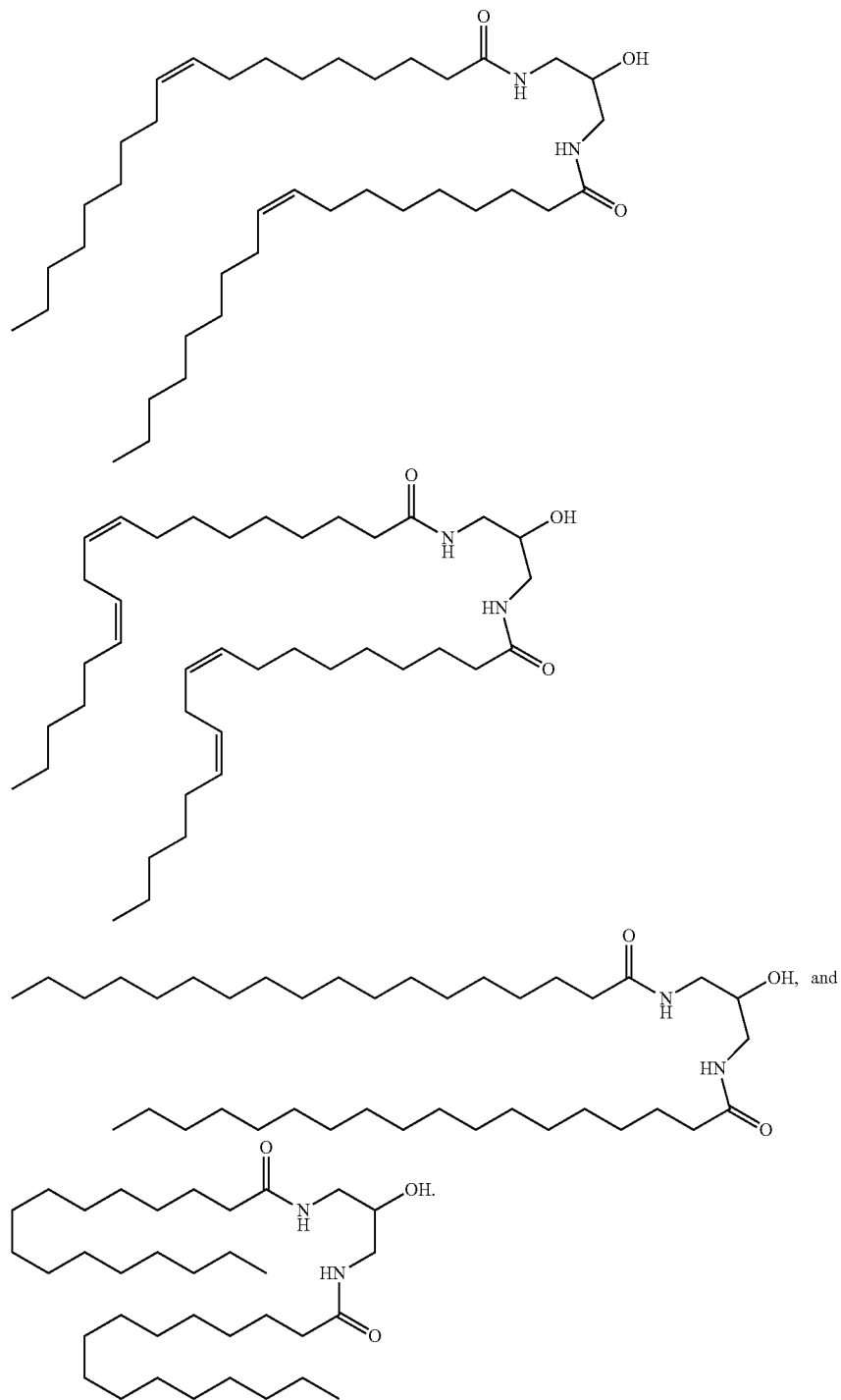

In another aspect, the present invention may be a composition for promoting hair growth or preventing hair loss further including a hair growth promoting component.

The hair growth promoting component may be a pyrimidine oxide derivative or a pharmaceutically acceptable salt thereof, but is not particularly limited.

When the pyrimidine oxide derivative is used as the hair growth promoting component, it promotes proliferation of hair follicular dermal papilla cells at a cellular level, and increases blood flow around the hair follicle, thereby promoting hair growth. It is possible to provide a composition containing the pyrimidine oxide derivative and the novel active compound represented by Chemical Formula 1 of the present invention, as the composite active component.

The composition containing the compound represented by Chemical Formula 1 and the pyrimidine oxide derivative mixed with each other according to the present invention helps to stimulate hair growth promoting factors of dermal papilla cells or keratinocyte cells to produce a hair shaft. Further, the composition stays below dermis, in particular, the pyrimidine oxide derivative is maintained or stays for a prolonged period of time in a hair bulb around which hair grows, thereby providing a remarkable effect on hair growth, such that there is a synergy effect for promoting hair growth or preventing hair loss.

Accordingly, when the compound represented by Chemical Formula 1 is used together with the pyrimidine oxide derivative in the composition according to an exemplary embodiment of the present invention, an effect of promoting hair growth may be significantly increased as compared to cases where the compound represented by Chemical Formula 1 are the pyrimidine oxide derivative, respectively, are used alone.

The pyrimidine oxide derivative used in the present invention is not particularly limited, but is more preferably any one or two selected from 6-(piperidinyl)-2,4-pyrimidinediamine-3-oxide represented by Chemical Formula 2 below or 2,4-diamino-6-pyrrolidino-pyrimidine-3-oxide represented by Chemical Formula 3 below since it is capable of extremely and remarkably promoting hair growth:

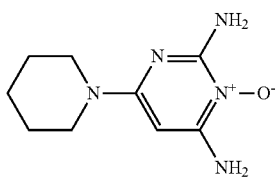

[Chemical Formula 2]

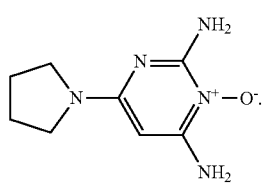

[Chemical Formula 3]

Further, when a salt of 6-(piperidinyl)-2,4-pyrimidinediamine-3-oxide or 2,4-diamino-6-pyrrolidino-pyrimidine-3-oxide among the pyrimidine oxide derivatives, or a mixture thereof is included as the active component, it is more preferred since it is possible to obtain an effect of inhibiting inflammation.

As an example of the present invention, the composition for promoting hair growth or preventing hair loss which is characterized by including the derivative represented by Chemical Formula 1 and the pyrimidine oxide derivative at 1:0.1 to 10 may be provided, but the ratio between the derivative represented by Chemical Formula 1 and the pyrimidine oxide derivative is not limited thereto.

When the composition is provided as a pharmaceutical composition, a cosmetic composition or a sanitary aid composition while having the above-described range, a hair growth effect may be the most excellent.

A method for preparing a derivative represented by Chemical Formula 1 which is an active component contained in the composition according to an exemplary embodiment of the present invention may include a step of reducing a temperature of a reaction solution containing 1,3-diamino-2-propanol, dichloromethane (DCM) and triethylamine to be 5 to −5° C. and then, adding oleic acid, palmitic acid or stearic acid, followed by stirring at room temperature for 3 to 5 hours, a step of stirring water and dichloromethane (DCM) to the reaction solution in which the stirring is finished, allowing to stand, followed by layer separation, and washing and drying an organic layer, and a step of recrystallizing a residue obtained after the drying to thereby obtain a white solid compound. In the method of preparing the compound 1, the derivative represented by Chemical Formula 1 may be prepared by adding oleic acid, palmitic acid or stearic acid. More preferably, it is the most effective to provide a composition containing the derivative of Chemical Formula 1 prepared by adding the oleic acid as the active component as the pharmaceutical composition, the cosmetic composition or the sanitary aid composition.

The composition according to an exemplary embodiment of the present invention may be provided as the pharmaceutical composition, the cosmetic composition or the sanitary aid composition.

In the formulation, the composition according to an exemplary embodiment of the present invention may be the skin external formulation or the hair external formulation, wherein the skin external formulation may include a form of solution, cream, ointment, paste, aerosol agent, gel or wax form, and the hair external formulation may include a form of shampoo, rinse, ampoule or treatment form.

In the skin external formulation, the skin may include all epidermis having hair root and hair follicles throughout the whole body of scalp, chins, armpits, the root of the ear, cheeks, eyebrows, etc. In the case of the hair external formulation, hair may include hair over the whole body such as hair, eyebrows (including eyelashes and eyebrows), beard, armpits, etc. Here, the external formulation may mean that the composition is directly applied to or distributed on the epidermis or hair. Here, the epidermis or hair may include epidermis or hair of mammal including human.

The composition according to an exemplary embodiment of the present invention may include the composite active component containing the material corresponding to Chemical Formula 1 and 6-(piperidinyl)-2,4-pyrimidinediamine-3-oxide or 2,4-diamino-6-pyrrolidino-pyrimidine-3-oxide among the pyrimidine oxide derivatives, a derivative of Chemical Formula 1, a salt of Chemical Formula 1 or a mixture thereof. The derivative or the salt is more preferred since they are capable of significantly promoting hair growth. Further, when the mixture thereof is included, it is more preferred since it is possible to obtain a damaged skin barrier recovery effect. Here, the derivative represented by Chemical Formula 1 may have a salt form.

When the composition according to an exemplary embodiment of the present invention is a pharmaceutical composition, the derivative represented by Chemical Formula 1 may be in a form of a pharmaceutically acceptable salt, and the pharmaceutically acceptable salt may refer to a salt prepared according to conventional methods in the art. Specifically, the pharmaceutically acceptable salt may include salts derived from inorganic acid and organic acid and bases that are pharmacologically acceptable or physiologically acceptable, but examples of the pharmaceutically acceptable salt are not limited thereto.

When the composition according to an exemplary embodiment of the present invention is a pharmaceutical composition, the composition may include a pharmaceutically acceptable carrier and/or excipient. The pharmaceutically acceptable carrier may be those conventionally used in the preparation of pharmaceutical composition. The carrier and/or excipient may be at least one selected from the group consisting of a binder, a glydent, a disintegrant, a lubricant, a coating material, an emulsifier, a suspension, a solvent, a stabilizer, an absorption aid, a water for injection, and an isotonic agent. In addition, the composition may further include a filler, an anti-coagulant, a lubricant, a wetting agent, a flavoring agent, an emulsifier, a preservative, etc. Here, the formulation may be a form of granule, powder, solution, cream, ointment, aerosol, paste, gel, wax, etc., and the solution may include a suspension state or an emulsion state as well as a state in which the active component is dissolved in a solvent.

When the composition according to an exemplary embodiment of the present invention is a pharmaceutical composition, an appropriate amount at which the composition is applied may vary depending on state and body weight, degree of disease of target to be applied, formulation, an application route, and duration of the composition. In the composition according to an exemplary embodiment of the present invention, the active component which is the composite active component containing the derivative represented by Chemical Formula 1, 6-(piperidinyl)-2,4-pyrimidinediamine-3-oxide, 2,4-diamino-6-pyrrolidino-pyrimidine-3-oxide among the pyrimidine oxide derivatives, or a mixture containing thereof, or a mixture thereof may be used at an application amount for one adult application of 20 $\mu l/cm^2$ per unit area of hair-removed skin, but the application amount is not limited thereto.

The application may be performed once to six times per day, and when the application is performed twice or more per day, each application may be performed at the same time interval, but is not particularly limited.

When the composition of the present invention is a cosmetic composition or a sanitary aid composition, the composition may contain adjuvants generally used for the cosmetic composition or the sanitary aid composition, for example, hydrophilic or lipophilic gelling agents, hydrophilic or lipophilic active agents, preservatives, antioxidants, solvents, fragrances, fillers, blocking agents, pigments, odor absorbing agents, dyes or mixtures thereof, in addition to the composite active component containing the derivative represented by Chemical Formula 1, and 6-(piperidinyl)-2,4-pyrimidinediamine-3-oxide, 2,4-diamino-6-pyrrolidino-pyrimidine-3-oxide among pyrimidine oxide derivatives, or a mixture thereof.

When the composition of the present invention is a cosmetic composition or a sanitary aid composition, the composition may be used into a formulation of cosmetics or sanitary aid. The sanitary aid formulation may be a form of granule, powder, solution, cream, ointment, aerosol, paste, gel, wax, etc., and the solution may include a suspension state or an emulsion state as well as a state in which the active component is dissolved in a solvent. The formulation of the cosmetics or the sanitary aid may be various such as solution, sol gel, emulsion, oil, wax, aerosol, etc., for example, hair tonic, hair cream, hair lotion, hair shampoo, hair rinse, hair conditioner, hair spray, hair aerosol, pomade, powder, gel, hair pack, hair treatment, eyebrow restorer, eyelash restorer, eyelash nutrient, pet shampoo, pet rinse, etc., but examples of the formulation are not limited thereto.

In addition, the composition according to an exemplary embodiment of the present invention may contain various components combined in general compositions for preventing hair loss or promoting hair growth so as to be appropriate for various formulations or final purposes. As an example, when the composition has a shampoo formulation, the composition may contain a synthetic surfactant which is a cleaning component and any one or more selected from preservatives, thickeners, viscosity modifiers, pH adjusters, fragrances, dyes, hair conditioning agents and water. The general various components combined in the general compositions for preventing hair loss or promoting hair growth so as to be appropriate for the above-described various formulations or final purposes are widely known to experts in the art.

The composition according to an exemplary embodiment of the present invention may be a composition for promoting hair growth or preventing hair loss, which contains the derivative represented by Chemical Formula 1, the pharmaceutically acceptable salt thereof, or the solvate thereof as 0.01 to 10 wt % of the active component. Preferably, for one to three applications per day, the composition may contain the active component in an amount of 0.01 to 8 wt %, more preferably 0.01 to 6 wt % to obtain a remarkable hair growth effect.

The composition according to an exemplary embodiment of the present invention may further contain glycol, C1-C5 lower alcohol, and water, but is not particularly limited thereto. The glycol may be at least one material selected from polyethylene glycol, polypropylene glycol, and polyethylene propylene glycol. The glycol may be prepared into paste, cream or gel formulations, and may improve moisture. The C1-C5 lower alcohol may be a solvent of the active component, and may be at least one material selected from methanol, ethanol, acetone, isopropyl alcohol, and n-butanol. The lower alcohol may have excellent volatility to promote the feeling when the composition is applied, and in particular, ethanol is more preferable since it has excellent volatility and is harmless to human body.

The composition according to an exemplary embodiment of the present invention may contain 5 to 20 parts by weight of glycol, 4 to 15 parts by weight of a lower alcohol, and 1 to 10 parts by weight of water, based on 1 part by weight of the active component. The weight ratio of the active component, the glycol, the lower alcohol and water is a range in which the hair growth effect is not hindered, skin irritation is inhibited during application, time necessary for uniform application is secured, a refreshment feeling is provided by appropriate volatilization, and absorption of the active component is promoted.

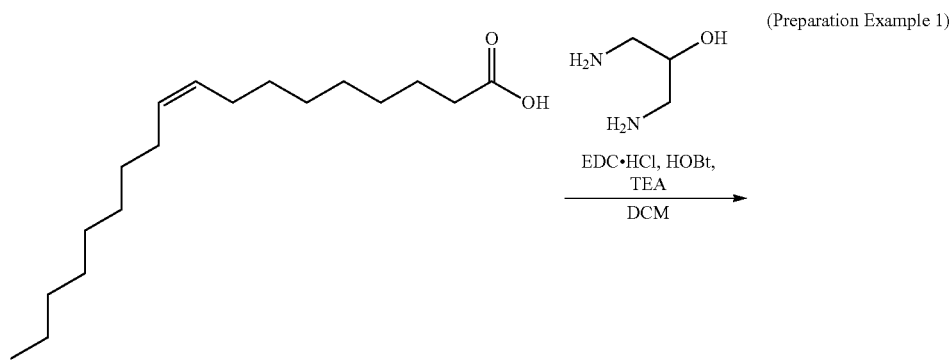

(Preparation Example 1)

-continued

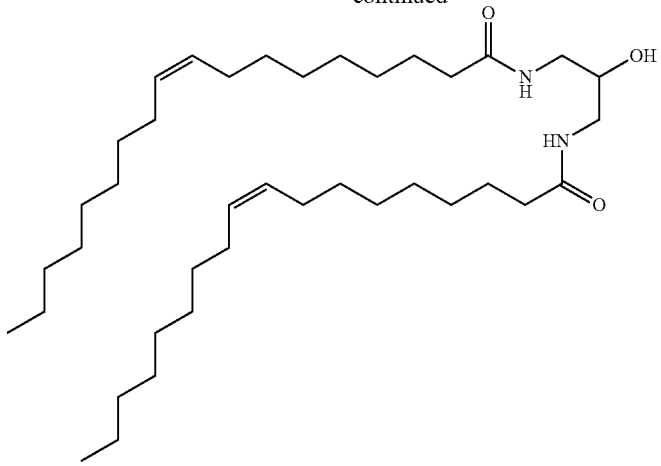

Dichloromethane (DCM, 500 ml, Samchun Pure Chemical) and triethylamine (TEA) (24.7 ml, Samchun Pure Chemical) were added to 1,3-diamino-2-propanol (3.99 g, 44.25 mmol, Sigma-Aldrich), thereby preparing a reaction solution. After 10 minutes at room temperature, EDC.HCl (25.45 g, 132.76 mmol, Sigma-Aldrich), HOBt (17.9 g, 132.76 mmol, Sigma-Aldrich), oleic acid (25.0 g, 88.51 mmol, Sigma-Aldrich) were added to the reaction solution, and stirred at room temperature for 4 hours. After stirring, dichloromethane (DCM) (500 ml) and water (500 ml) were added to the reaction solution, and the resultant mixture was stirred and allowed to stand, followed by layer separation. All organic layers of the reaction solution were acidified with concentrated hydrochloric acid, stirred for 5 minutes, and then neutralized with a saturated aqueous solution of hydrogen chloride. The organic layers were collected and washed with brine (150 ml), and dried over magnesium sulfate ($MgSO_4$), and filtered, and the filtrate was concentrated under reduced pressure. The residue was recrystallized with methanol (100 ml) to obtain a white solid compound (23 g, yield: 84%). The MS and NMR results of the obtained solid (named '056N') are as follows.

MS (ESI pos. ion) m/z: 620 ($MH^+$). $^1$H NMR (600 MHz, $CDCl_3$): 6.36-6.34 (m, 2H), 5.37-5.31 (m, 4H), 4.25 (br s, 1H), 3.78-3.75 (m, 1H), 3.38-3.27 (m, 4H), 2.22 (t, J=7.8 Hz, 4H), 2.01 (q, J=6.0 Hz, 8H), 1.68-1.60 (m, 5H), 1.33-1.27 (m, 39H), 0.88 (t, J=7.2 Hz, 6H).

EXAMPLE 1

A composition was prepared using a composite active component containing '056N' prepared in Preparation Example 1 and a pyrimidine oxide derivative. In detail, the composition for hair growth was prepared by mixing 1 wt % of '056N', 2 wt % of pyrrolidinyl diaminopyrimidine oxide (2,4-diamino-6-pyrrolidino-pyrimidine-3-oxide) (Kumar), 60 wt % of ethanol, and 37 wt % of polypropylene glycol (Mw=76.09).

Evaluation of Hair Growth Characteristic

An in-vivo evaluation using an experimental animal, which is mainly used for hair growth and hair fostering effects, was performed. C57BL/6 mice were used as experimental animals. The C57BL/6 mice are animal models which are the most widely used for testing hair growth and have a characteristic period in which hair enters into catagen from 6 weeks after birth, and into telogen from 7 weeks after birth, and goes back to anagen at 12 weeks after birth.

Six-week-old female C57BL/6 mice were purchased, and had an adaptation period of about 1 week under breeding conditions of 23±3° C., relative humidity of 55±10%, and illumination time for 12 hours, and then, were tested when the mice were 7 weeks old. The mice were anesthetized for 1 minute in a desiccator containing ether, and then, hair on the back part thereof was removed by using a depilator. After 1 day, the composition for hair growth prepared in Preparation Example 1 was applied on the mouse with an unscathed back. The prepared composition for hair growth was applied once a day, and for one application, the composition was applied in an amount of 20 µL/$cm^2$ per unit area of hair-removed skin.

Then, change in color of the applied part was observed by taking images at an interval of one week.

As a Comparative Example, only the vehicle (PEG: EtOH=7:3) was applied once a day in the same amount as the composition for hair growth.

FIG. 1 illustrates observations of the mouse immediately before the test (left image) and the mouse when the composition was applied for 8 weeks (right image), and specifically, FIG. 1(a) illustrates the mouse after the vehicle was applied (right image), and FIG. 1(b) illustrates the mouse after the composition for hair growth prepared in Example 1 was applied (right image). It could be appreciated from the results of FIG. 1 that the composition for hair growth according to the present invention had extremely high hair growth activity.

Skin Barrier Damage Recovery Test

The present experiment was performed in order to figure out effects of the composition according to the present invention on skin barrier recovery after damaging skin barrier of a nude mouse. Right and left epidermis of the nude mouse were damaged by using D-Squame. Here, transepidermal water loss (TEWL) was measured and maintained so that there was no difference in values. Then, the composition for hair growth prepared in Example 1 including 0.5 wt % of O56N as the active component was applied. For Comparative Example, the vehicle (PEG:EtOH=7:3) was applied in the same amount of the composition for hair growth. The TEWL was measured in 3 hours and 6 hours after the application to measure a barrier recovery ability. As a result of the measurement, the barrier recovery ability of the mouse applied with the composition for hair growth prepared in Example 1 was measured faster than that with the vehicle alone. Results thereof were shown in FIG. 2. It could be confirmed that the composition of the present invention is effective for skin barrier recovery.

Hereinabove, although the present invention is described by specific matters, limited exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scopes and spirits of the invention.

The invention claimed is:

1. A composition for promoting hair growth or preventing hair loss comprising:
   a derivative represented by Chemical Formula 1 below as an active component:

[Chemical Formula 1]

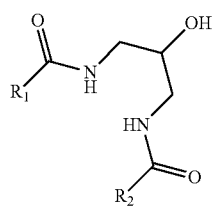

in Chemical Formula 1,
   $R_1$ and $R_2$ are linear or branched (C7-C30)alkenyl or (C7-C30)alkynyl, wherein the alkenyl or alkynyl may be further substituted with hydroxy, carbonyl, (C1-C30)aryl, (C1-C30)aryloxy, (C1-C30)alkylamino, di(C1-C30)alkylamino or amino(C1-C30)alkyl,
   wherein the composition further comprises a pyrimidine oxide derivative or a pharmaceutically acceptable salt thereof, wherein the pyrimidine oxide derivative is any one or two selected from 6-(piperidinyl)-2,4-pyrimidinediamine-3-oxide represented by Chemical Formula 2 below and 2,4-diamino-6-pyrrolidino-pyrimidine-3-oxide represented by Chemical Formula 3 below:

[Chemical Formula 2]

[Chemical Formula 3]

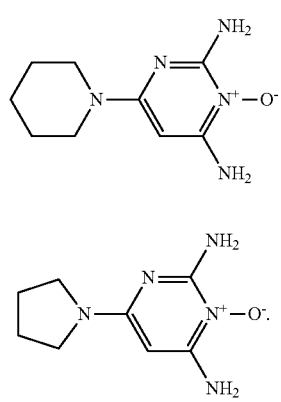

2. The composition of claim 1, wherein the sum of the number of carbons of $R_1$ and $R_2$ is 14 to 50.

3. The composition of claim 1, wherein the Chemical Formula 1 is selected from the following compounds:

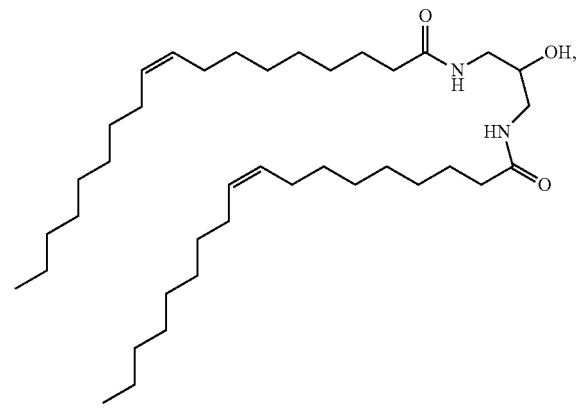

and

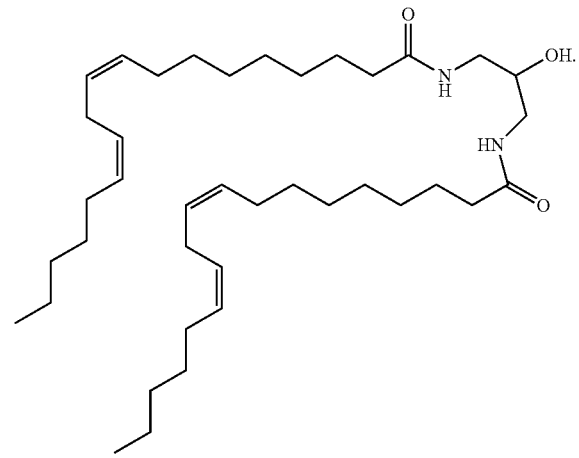

4. The composition of claim 1, wherein the derivative represented by Chemical Formula 1 and the pyrimidine oxide derivative are included at 1:0.1 to 10 (weight ratio).

5. The composition of claim 4, wherein the composition contains the derivative represented by Chemical Formula 1 as 0.01 to 10 wt % of the composition.

6. The composition of claim 1, wherein the composition is a pharmaceutical composition or a cosmetic composition.

7. The composition of claim 6, wherein the composition is a skin external formulation including solution, cream, ointment, paste, aerosol agent, gel or wax form, or a hair external formulation including shampoo, rinse, or ampoule.

* * * * *